United States Patent [19]

Salo et al.

[11] Patent Number: 5,417,717

[45] Date of Patent: May 23, 1995

[54] IMPLANTABLE CARDIAC FUNCTION MONITOR AND STIMULATOR FOR DIAGNOSIS AND THERAPY DELIVERY

[75] Inventors: Rodney W. Salo, Fridley; Bruce A. Tockman, Minneapolis; Morton M. Mower, Edina, all of Minn.

[73] Assignee: Cardiac Pacemakers, Inc., St. Paul, Minn.

[21] Appl. No.: 243,069

[22] Filed: May 16, 1994

Related U.S. Application Data

[63] Continuation of Ser. No. 112,181, Aug. 25, 1993, abandoned, which is a continuation of Ser. No. 787,052, Nov. 4, 1991, abandoned.

[51] Int. Cl.$^6$ ............................................. A61N 1/365
[52] U.S. Cl. ...................................... 607/18; 607/23; 607/24; 607/3
[58] Field of Search ..................... 607/3, 2, 24, 9, 17, 607/18, 23; 623/3; 600/16, 17; 128/734

[56] References Cited

U.S. PATENT DOCUMENTS

| | | | |
|---|---|---|---|
| 4,686,987 | 8/1987 | Salo et al. | 128/419 PG |
| 4,730,619 | 3/1988 | Koning et al. | 128/419 PG |
| 4,735,205 | 4/1988 | Chachques | 128/419 PG |
| 4,773,401 | 9/1988 | Citak et al. | 128/419 PG |
| 4,867,160 | 9/1989 | Schaldach | 128/419 PG |
| 4,936,304 | 6/1990 | Kresh et al. | 128/419 PG |
| 5,058,583 | 10/1991 | Geddes et al. | 128/734 |
| 5,067,960 | 11/1991 | Grandjean | 600/16 |
| 5,069,680 | 12/1991 | Grandjean | 600/16 |
| 5,154,171 | 10/1992 | Chirife | 128/419 PG |
| 5,174,286 | 12/1992 | Chirife | 128/419 PG |

OTHER PUBLICATIONS

Stevens, Larry, Stephen F. Badylak, Wolfgang Janas, Mary Gray, Leslie A. Geddes and William D. Voorhees III, "A Skeletal Muscle Ventricle Made from Rectus Abdominus Muscle in the Dog", *Journal of Surgical Research*, 46: 84–89 (1989).

Chachques, J. C., P. A., Grandjean, P. Perier, P. Nataf, C. Acar, S. Mihaileanu, D. Bensasson, J. P. Kieffer, B. Abry, J. N. Fabiani, A. Deloche, P. Blondeau et A. Carpentier, "Cardiomyoplastie". *Arch. Mal. Coeur.* 82: 919–926 (1989).

Chiu, Ray C.-J., Garrett L. Walsh, Michael L. Dewar, Jean-H. De Simon, Aioda S. Khalafalla and David Ianuzzo, "Implantable Extra-Aortic Balloon Assist Powered By Transformed Fatique-Resistant Skeletal Muscle". *J. Thorac Cardiovasc. Surg.* 94(5): 694–719 (Nov. 1987).

(List continued on next page.)

*Primary Examiner*—William E. Kamm
*Assistant Examiner*—Kennedy J. Schaetzle
*Attorney, Agent, or Firm*—Haugen and Nikolai

[57] ABSTRACT

An implantable monitor/stimulator is disclosed that monitors and assesses indices of cardiac function, including the strength and timing of cardiac contraction, then automatically executes a physician-selected mode of therapy. It accomplishes this by assessing impedance, electrocardiogram, and/or pressure measurements, then calculating various cardiac parameters. The results of these calculations may be stored within the device, telemetered to an external monitor or display and/or may be used by the physician to determine the mode of therapy to be chosen. If indicated, therapy is administered by the device itself or by telemetering control signals to various peripheral devices for the purpose of enhancing either contraction or relaxation of the heart. The cardiac parameters that are calculated all provide an assessment of level of cardiac function by monitoring changes in ventricular filling and ejection or by calculating isovolumic phase indices of heart contraction. Examples of such parameters are ejection fraction, cardiac output, stroke work, and/or various pressure-volume relationships. These parameters determine the mode of therapy that will be selected by a physician. Choices of therapy include several forms of pacing of cardiac or skeletal muscle, and telemetry to implanted or external units for drug infusion or for monitoring by a central data system.

18 Claims, 4 Drawing Sheets

OTHER PUBLICATIONS

Acker, Michael A., William A. Anderson, Robert L. Hammond, Alvin J. Chin, James W. Buchanan, Cynthia C. Morse, Alan M. Kelly, and Larry W. Stephenson, "Skeletal Muscle Ventricles in Circulation", *J Thorac Cardiovasc Surg.* 94(2):163–174 (Aug. 1987).

Chachques, J. C., P. A. Grandjean, J. J. Tommasi, P. Perier, S. Chauvaud, I. Bourgeois and A. Carpentier, "Dynamic Cardiomyoplasty: A New Approach To Assist a Chronic Myocardial Failure", *Lead Support Systems.* 5: 323–327 (1987).

Sagawa, Kiichi, Hiroyuki Suga, Artin A. Shoukas, Kenneth M. Bakalar, "End-Systolic Pressure/Volume Ratio: A New Index of Ventricular Contractility". *The American Journal of Cardiology.* 40: 748–753 (Nov. 1977).

Glantz, Stanton A., "A Constitutive Equation for the Passive Properties of Muscle". *J. Biomechanics.* 7: 137–145 (1974).

IMPLANTABLE CARDIAC FUNCTION MONITOR AND STIMULATOR FOR DIAGNOSIS AND THERAPY DELIVERY

This is a continuation of application Ser. No. 08/112,181, filed on Aug. 25, 1993, now abandoned, which is a Continuation of application Ser. No. 07/787,052 filed on Nov. 4, 1991, now abandoned.

BACKGROUND OF THE INVENTION

I. Field of the Invention

This invention relates generally to the design of cardiac stimulating devices and, more particularly, to an implantable monitor/stimulator that monitors and assesses level of cardiac function then permits a physician to arbitrate the therapy mode, if therapy is indicated. It accomplishes this by assessing impedance, electrocardiogram, and/or pressure measurements, then calculating various cardiac parameters. The results of these calculations determine the mode of therapy to be chosen, then therapy may be administered by the device itself or a control signal may be telemetered to various peripheral devices aimed at enhancing the heart's function. Alternatively, the device may be programmed to monitor and either store or telemeter information without delivering therapy.

II. Discussion of the Prior Art

Patients suffering from chronic congestive heart failure manifest an elevation of left ventricular end-diastolic pressure, according to the well-known heterometric autoregulation principles espoused by Frank and Starling. This may occur while left ventricular end-diastolic volume remains normal due to a decrease in left ventricular compliance concomitant with increased ventricular wall stiffness. Prior attempts to increase wall contractility and thus improve cardiac performance have focused on drug therapy and cardiomyostimulation.

Many inotropic drugs have recently become available, targeted at various receptors in the ventricular walls and designed for the purpose of directly stimulating cardiac tissue in order to increase contractility. However, there exist many possible undesirable side effects, in addition to the fact that these drugs do not always work for their intended purpose. This is especially characteristic of the patient suffering from end-stage heart failure. Because of these problems with drug efficacy, the techniques of adaptive rate cardiac pacing and cardiomyostimulation have been developed.

The performance of adaptive rate cardiac pacemakers has advanced greatly in recent years. Such pacers sense the presence or absence of intrinsic cardiac electrical activity, or other physiologic parameter, and then respond only by increasing or supporting heart rate by direct stimulation of cardiac tissue. The heart rate response may also be based on the sensing of some type of physiologic need but, to date, no implantable device has been proposed to directly evaluate cardiac function and then deliver appropriate therapy designed to improve function. Although adaptive rate pacing may increase cardiac output by increasing heart rate, it has not been indicated as a therapy in heart failure because neither contraction nor relaxation are improved, and conversely, increased myocardial oxygen demands may ensue. The only application of pacing technology to address heart failure has been in the area of cardiomyoplasty, where electrical stimulation is directed towards some type of skeletal muscle system to augment cardiac function.

Cardiomyostimulation is a technique intended to increase cardiac output, in order to assist a compromised heart. As disclosed in U.S. Pat. No. 4,735,205, issued to Chachques, skeletal muscle can be trained to withstand the rigor of long-term sequential contraction without undue fatigue. When such trained muscle is surgically wrapped around the ventricles then sequentially electrically stimulated using demand-type cardiac pacer circuitry, mechanical assistance is provided for compromised contraction. This occurs because stimulated contraction of this skeletal muscle causes constriction upon the ventricles and forces blood into the arterial system. Although this process has proven to be useful, it does not directly affect contractile forces within the heart itself and is known to impair diastolic function by increasing ventricular chamber "stiffness".

Despite the improvements in treatment described above, there remains a large group of patients for whom these approaches either do not work or are contraindicated for other medical reasons. The present invention is intended to enhance contractility or relaxation in this group of patients by providing an apparatus that monitors cardiac function and then directly stimulates ventricular tissue in a way that optimizes the functional parameter or parameters under control.

Impedance-based measurements of cardiac parameters such as stroke volume are known in the art. U.S. Pat. No. 4,674,518, issued to Salo, discloses an impedance catheter having plural pairs of spaced surface electrodes driven by a corresponding plurality of electrical signals comprising high frequency carrier signals. The carrier signals are modulated by the tidal flow of blood in and out of the ventricle. Raw signals are demodulated, converted to digital, then processed to obtain an extrapolated impedance value. When this value is divided into the product of blood resistivity times the square of the distance between the pairs of spaced electrodes, the result is a measure of blood volume held within the ventricle. These calculations may be made using spaced sensors placed within a catheter, as in the Salo '518 patent, or they may be derived from signals originating in electrodes disposed in the heart, as described in U.S. Pat. No. 4,686,987, issued to Salo and Pederson. The device of the '987 patent senses changes in impedance to determine either ventricular volume or stroke volume (volume of blood expelled from the ventricle during a single beat) to produce a rate control signal that can be injected into the timing circuit of another device, such as a cardiac pacer or drug infusion pump. In this manner, the rate of operation of the slaved device may be controlled. An example of application of this impedance sensing circuitry to a demand-type cardiac pacer is disclosed in U.S. Pat. No. 4,773,401, issued to Citak, et al. Other devices may combine impedance sensing with internal pressure measurement as disclosed in U.S. patent application Ser. No. 07/490,392 of Salo, and with telemetry as disclosed in U.S. Pat. No. 4,562,841, issued to Brockway, et al.

The present invention combines these approaches, rendering a device that detects and monitors levels of cardiac function and delivers therapy on the basis of this monitored information. The primary mode of delivery is direct electrical stimulation, resulting in improved contractility, relaxation or improved cardiac output.

OBJECTS

It is accordingly a principal object of the present invention to provide an implantable apparatus for applying therapy to strengthen cardiac contractions having means for detecting and measuring one or more cardiac hemodynamic parameters, including internal electrocardiogram, intracardiac impedance and/or internal pressure, whereby either systolic or diastolic cardiac function can be enhanced by direct electrical stimulation.

It is a further object of the present invention to provide an implantable apparatus for applying therapy to a patient's heart which is capable of measuring cardiac hemodynamic parameters then delivering therapy to augment or improve these cardiac parameters.

It is yet another object of the present invention to provide an implantable apparatus which implements various electrical stimulation modalities to enhance a heart's contractile state, including enhancement of contractility, relaxation or cardiac output.

SUMMARY OF THE INVENTION

The present invention monitors pressure and/or impedance to assess short or long-term changes in level of cardiac function. Particularly, the implantable device monitors conventional parameters of cardiac function and contractile state, including all phases of the cardiac cycle. Thus, assessments of contractile state measured by the device include indices of both cardiac relaxation and contraction. Utilizing the dual source ventricular impedance plethysmography technique described in U.S. Pat. No. 4,674,518, issued to Salo, the present invention monitors cardiac function by assessing hemodynamic changes in ventricular filling and ejection or by calculating isovolumic phase indices by known algorithms. The primary calculations involve:

(1) the time rate of change in pressure or volume, dP/dt or dV/dt, as isovolumic indicators of contractility;
(2) ejection fraction as an ejection phase index of cardiac function according to the known quotient of stroke volume divided by end diastolic volume;
(3) Maximal elastance, $E_{MAX}$,
(4) regression slope through maximal pressure-volume points as a further ejection phase index of contractility using the method of Sagawa;
(5) stroke work according to the known pressure-volume integration;
(6) the time course of minimum (end) diastolic pressure-volume measurements according to the method of Glantz as a measure of diastolic function; and
(7) cardiac output calculation according to the known product of heart rate and stroke volume as an index of level of global function.

To accomplish these calculations, some necessary values may be prestored in an auxiliary memory as criteria ranges or as input patient baseline data.

BRIEF DESCRIPTION OF THE DRAWING FIGURES

These together with other objects and advantages, which will become subsequently apparent reside in the details of construction and operation of a preferred embodiment, as more fully hereinafter described and claimed, reference being had to the accompanying drawings forming a part hereof, wherein like numerals refer to like parts throughout.

DETAILED DESCRIPTION OF THE PREFERRED EMBODIMENT

Figure 1:
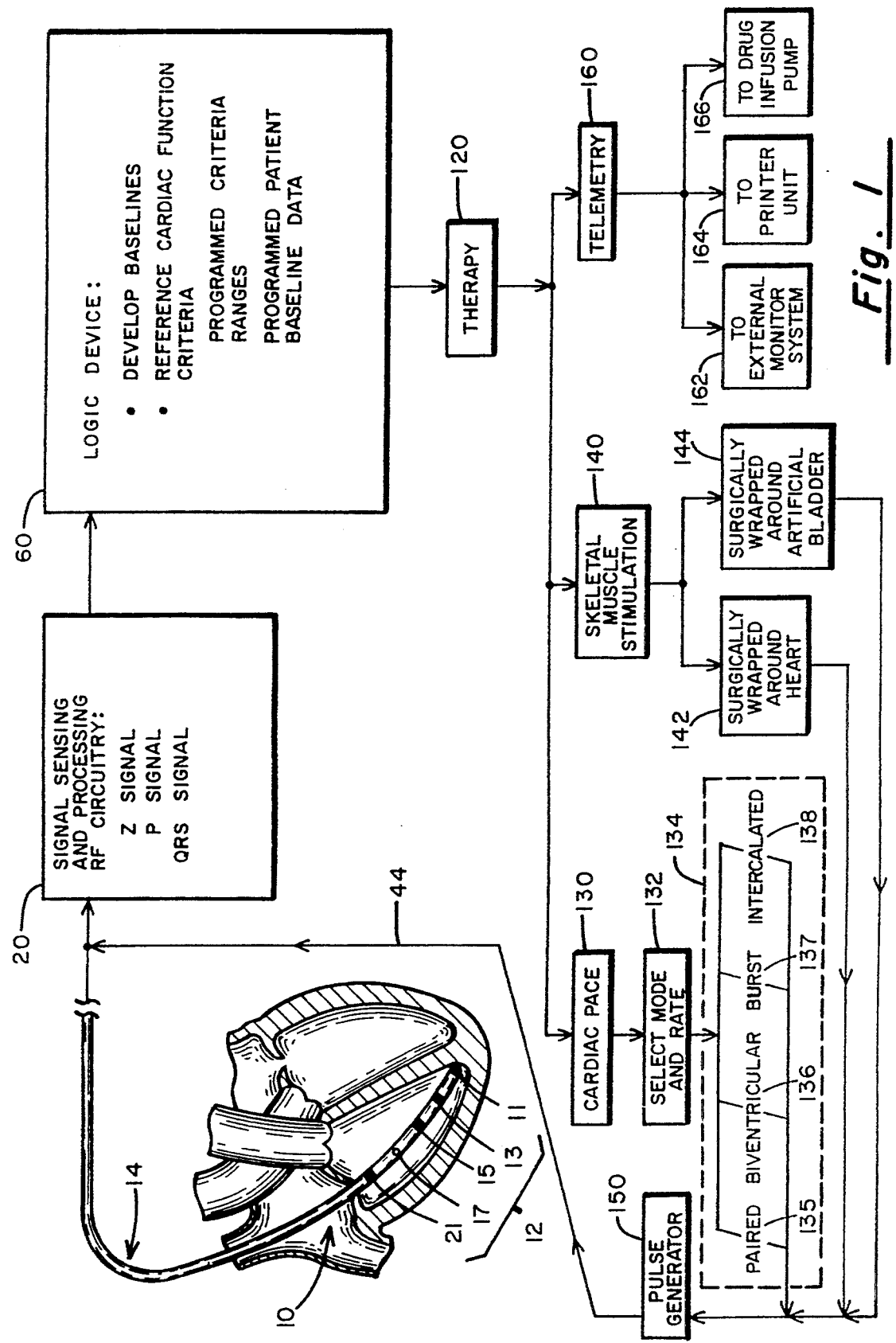
FIG. 1 is a functional block diagram of a preferred apparatus for implementing the present invention.

Referring to FIG. 1, a preferred embodiment of the stimulating apparatus incorporating the present invention is shown by means of a block diagram. It is comprised of intracardiac sensing apparatus, denoted generally as 10, hemodynamic signal processing means 20 coupled to the sensing apparatus, a logic device 60 and a physician selectable therapy mode means, denoted generally as block 120.

Figure 2:
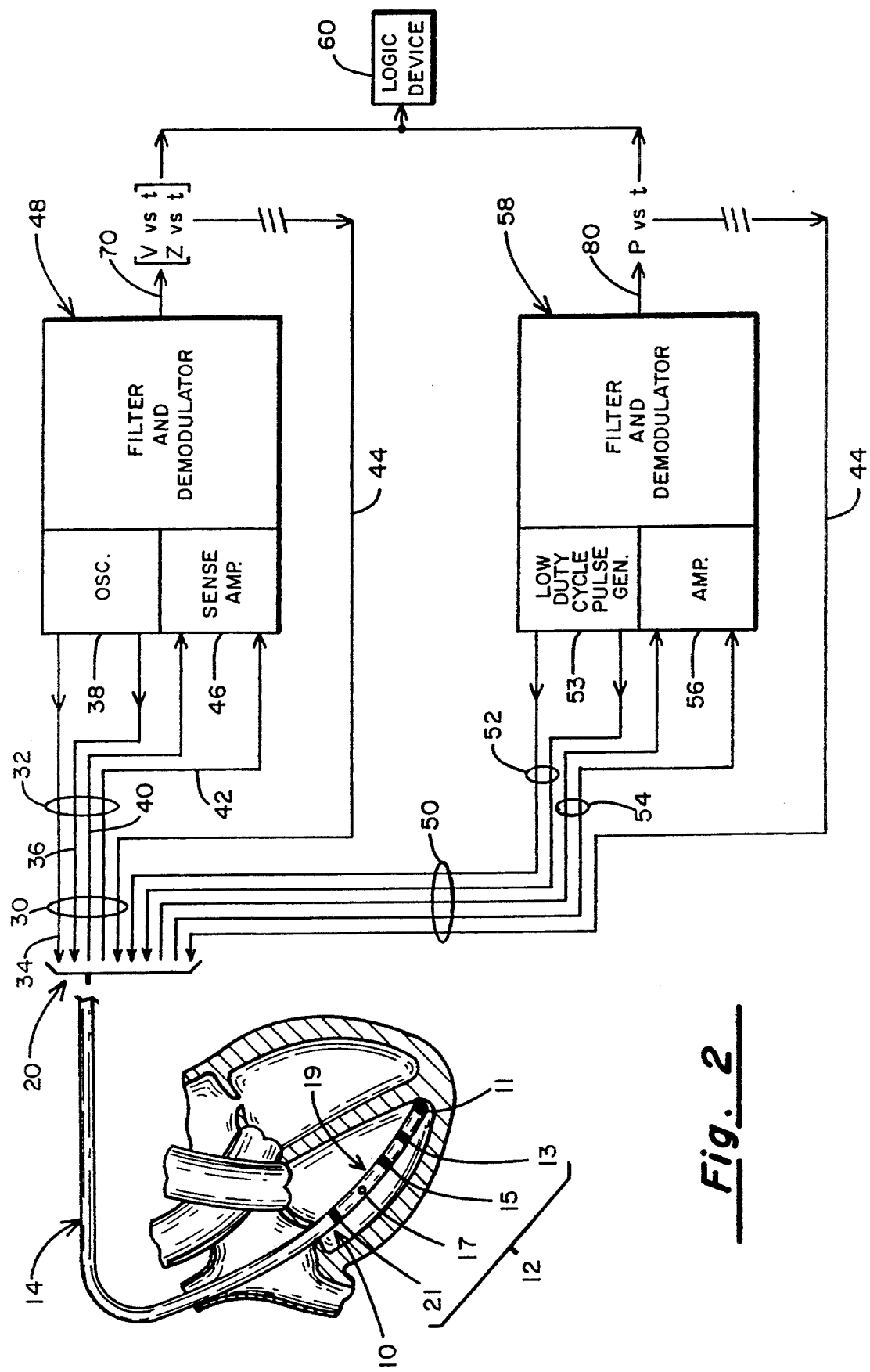
FIG. 2 shows placement of multiple sensors within the right ventricle of the heart and a block diagram of the signal processing circuitry used in practicing the invention.

The sensing apparatus 10 and associated circuitry shown in FIG. 2 may be similar to the systems disclosed in U.S. Pat. No. 4,674,518, issued to Salo; U.S. Pat. No. 4,686,987, issued to Salo, et al.; and U.S. patent application Ser. No. 07/490,392, issued to Salo, et al.; all assigned to Applicant's assignee. As such, it comprises intracardiac sensing means 12 and associated drive circuitry 20. A plurality of electrodes placed in or on the heart are used to derive impedance signals. In addition, or alternatively, sensing and drive circuitry for a piezoelectric transducer may be used to derive pressure versus time signals, as described in detail hereafter.

The signal sensing and processing unit 20 (FIG. 1), receives the raw hemodynamic signal from the sensing/stimulating lead apparatus 12 and contains amplification, filtering and demodulation circuitry. The resulting signals appear as waveforms of impedance versus time, pressure versus time or as standard electrocardiography PQRST waveforms. This signal is forwarded to logic circuitry (Block 60) for further processing, as also described in greater detail hereinafter.

The logic device 60, may comprise a microprocessor of conventional design having data storage means, an arithmetic/logic unit and an A/D converter, which operate under control of a stored program. It receives the filtered and demodulated signals from the sense unit 20 via lines 30 and 50 (FIG. 2), then processes them in a manner that is a combination of the methods disclosed in the aforereferenced U.S. patent application Ser. No. 490,392 and U.S. Pat. Nos. 4,674,518 and 4,686,987. Logic device 60 includes a memory (FIG. 3) for storing baseline values and references relating to cardiac function criteria. Also stored for reference by the microprocessor are patient baseline data that are sampled at various intervals. Physician inputs to the microprocessor via a keyboard or the like are used to manually select a mode of therapy, as indicated by block 120.

The various therapies available, as represented generally by block 130 for pacing, 140 for skeletal muscle stimulation and 160 for telemetry, are all described more fully hereinafter. These include the adoption of various cardiac pacing modes (Block 134), skeletal muscle stimulation (Blocks 142 and 144) and externally provided therapies directed from the implanted device via telemetry apparatus (Blocks 162, 164 and 166). All are focused upon improving function of the heart by means of selective timing of electrical stimuli to the myocardium or other tissue, or by the automatic infusion of an appropriate drug. This is in contrast to conventional cardiac pacing which typically senses the absence of intrinsic cardiac activity and simply stimulates the occurrence of a contraction, or standard rate-adaptive pacing systems which monitor independent non-cardiac variables in order to provide some rate response to exercise. These various therapies are either administered through the same internal lead that sensed the original signal or are administered via auxiliary electrodes placed on the heart or other muscle or via external systems that receive a signal telemetered to them by the implantable device of the present invention.

Turning to the elements of FIG. 1 with greater particularity, the sense apparatus and circuitry 10 is based upon an impedance plethysmography technique, such as that disclosed in the aforereferenced Salo U.S. Pat. No. 4,674,518 and Salo, et al. U.S. Pat. No. 4,686,987 patents. These techniques utilize measurement of intracardiac impedance, specifically, measurement of impedance in the right ventricle. An intracardiac impedance waveform containing information relating to stroke volume as well as to frequency and depth of respiration is obtained from a set of electrodes, designated generally as 12, and which are disposed on the surface of a catheter or lead 14 and connected by conductors within the lead body to the signal processing circuitry 20.

Shown in greater detail in FIG. 2 and as disclosed in our earlier U.S. Pat. No. 4,686,987, the catheter or lead 14 is intended to be inserted into the right ventricle of the heart. One possible electrode configuration is shown as being mounted to the surface of this lead 14, where, for example, a pair of drive electrodes 11 and 21 and a pair of sense electrodes 13 and 15 are shown connected to signal processing means 20 by the conductors generally designated as 32. Electrical conductors 34 and 36 couple the drive electrodes 11 and 21 to a carrier oscillator circuit 38 contained in signal processor 20. Electrical conductors 40 and 42 couple the sense electrodes 13 and 15 to a sensing amplifier 46, also contained in signal processor 20. A filter and demodulator circuit 48 receives the signal from the sense amplifier 46 and contains circuitry to amplify, filter and demodulate the signal before further processing by the logic device (Block 60). The circuitry at block 48 creates a time-dependent signal proportional to intracardiac impedance (Z v. t) on line 70. It is then in proper form for processing in accordance with the algorithms defined by the programs contained in the logic device (Block 60). To provide electrical stimulation, there is provided a pulse generator 150 whose output is connected by conductor 44 in the catheter 14 to the stimulating tip electrode 11.

The technique of the present invention may also utilize a pressure sensitive, solid-state pressure transducer 17 positioned near the distal end of an endocardial lead 14 to directly monitor hemodynamic changes, such as variation in pressure within the right ventricle. Utilizing methods known in the art, a pressure versus time signal (P v. t) is obtained on line 80, which reveals excursions due to normal systolic and diastolic pressure variations, and which are contaminated by low frequency variations which correspond to intrathoracic pressure changes attendant to normal respiratory processes. As explained in the Salo, et al. application Ser. No. 490,392, a clean signal may be obtained by using a signal processing means 58 which provides pressure variations on a beat-by-beat basis. Appropriate filtering is used to extract the period of the respiratory signal and its peak-to-peak amplitude (tidal volume).

Specifically, a commercially available microminiature pressure transducer 17 is mounted within the endocardial lead 14. Such a pressure transducer typically comprises a chemically etched silicon diaphragm onto which a piezoelectric resistive crystal has been mounted. Wiring connects the crystal transducer to external circuitry for processing the pressure modulated carrier signal. For protection, this transducer 17 is typically mounted behind a compliant membrane which covers a window opening 19. The window 19 is positioned near the distal end of the endocardial lead 14.

Mechanical variations in pressure within the ventricle are monitored and converted into electrical signals which depict the amplitude changes of the pressure waves advancing toward the transducer head. This may be accomplished by a simple Wheatstone bridge circuit or other known circuitry. Within the pressure signal processing apparatus (FIG. 2), a low duty cycle pulse generator 53 sends pulsatile alternating current toward the transducer head via conductors 52. The signal from the energized crystal (not shown) is then carried via conductors 54 to amplifier 56. The signal processing circuit 58 receives the signal from the amplifier 56 and contains circuitry to filter and demodulate the signal to create a time-dependent signal proportional to intracardiac pressure. After such extraction of the modulation envelope and removal of the carrier, the microprocessor-based logic device (Block 60), shown in detail in FIG. 3, receives the signal on line 80, which then is in proper form for processing.

Figure 3:
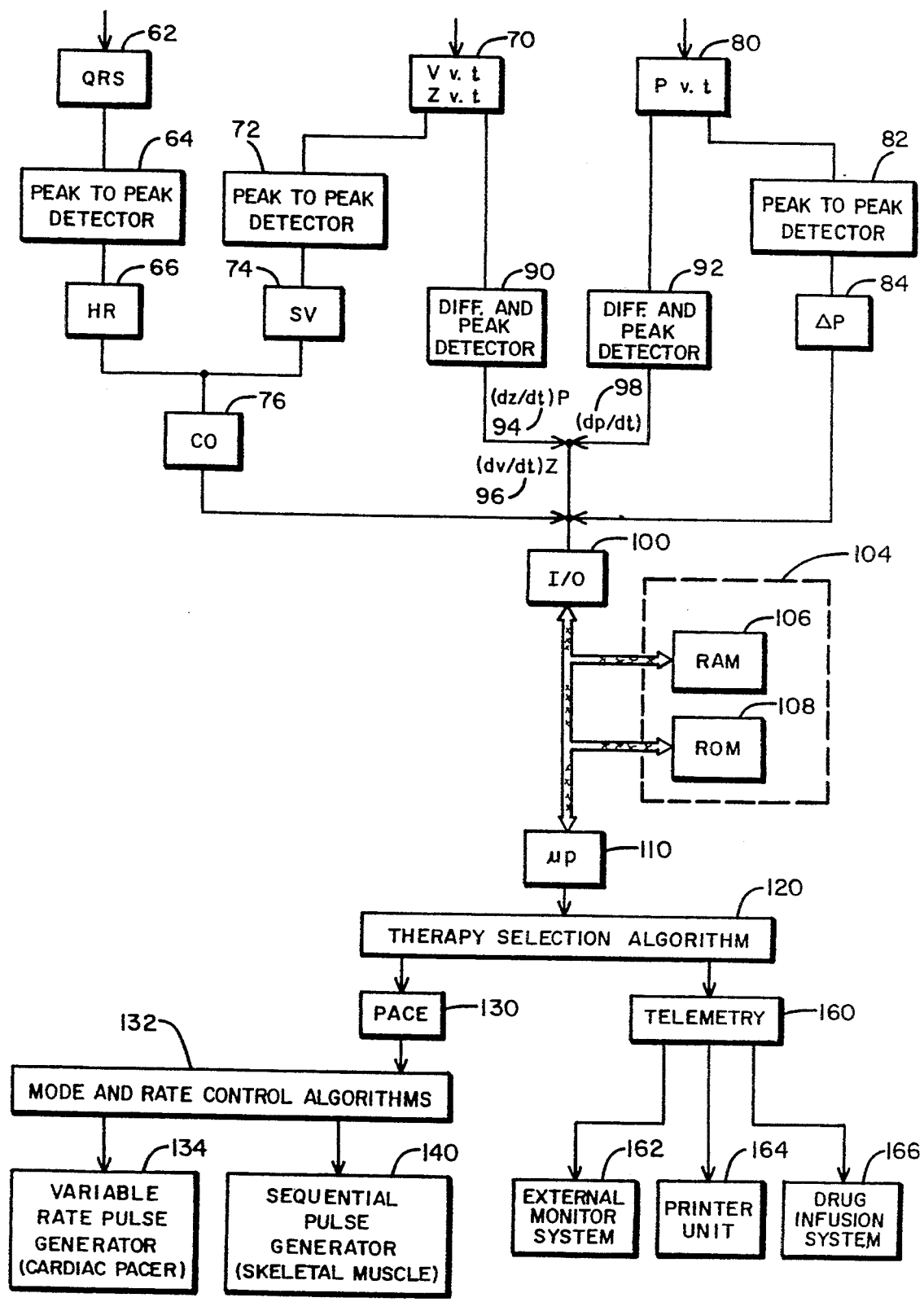
FIG. 3 is a diagram illustrating the "logic device" section of FIGS. 1 and 2.

Turning to the block diagram of FIG. 3, the parallel manner in which the Z v. t and P v. t waveforms are processed within logic device 60 becomes evident. These processes, as well as processing of the electrocardiogram signal (Block 62), are described in detail in U.S. Pat. Nos. 4,674,518 (Salo), 4,686,987 (Salo, et al.) and 4,773,401 (Citak, et al.) as well as in application Ser. No. 07/490,392 (Salo). Application of the electrocardiogram signal (Block 62) to a peak-to-peak detector (Block 64) yields a signal that is proportional to heart rate (HR) at block 66. Application of the Z v. t signal (Block 70) to a peak-to-peak detector (Block 72) yields a signal that is proportional to the heart's stroke volume (SV) per beat at block 74. Application of the P v. t signal, as at block 80, to a peak-to-peak detector (Block 82) yields a signal at block 84 that is proportional to the change in pressure (AP) that occurs as the heart beats. From the buffers providing the HR (Block 66) and SV (Block 74) data, cardiac output (CO) can be calculated as the product of HR×SV, as indicated by block 76. This value is useful as an index of global function, relating to performance of the entire heart as a unit, as opposed to the regional function of, for example, one ventricle.

Differentiator and peak detector circuits, as at blocks 90 and 92, produce signals that are proportional to the positive or negative peak value of the differentiated waveform, whether impedance, volume or pressure (Lines 94, 96, 98). These measures are known indices of systolic or diastolic function.

Further calculation of ejection fraction and stroke work may also be performed at this stage by a microprocessor (Block 110). A conventional input/output (I/O) device (Block 100) receives the HR (Block 66), SV (Block 74), CO (Block 76), AP (Block 84), dZ/dt (Line 94), dV/dt (Line 96) and dP/dt (Line 98) signals for storage in memory devices 104 using RAM 106 or ROM 108, or for further processing in microprocessor 110. Ejection fraction (EF) is computed by dividing the stroke volume (SV) signal (Block 74) by end-diastolic volume (EDV). Stroke work (SW) is derived by integrating the area within the curve defined by a plot of pressure v. volume as the heart contracts and expands. A further ejection phase index of contractility may be derived from the slope of a regression line passing through maximal pressure-volume points that are plotted for sequential beats, which yields a characteristic end-systolic pressure-volume relation that may be compared to desirable known ranges. Alternatively, the stroke work may be plotted against end diastolic volume and the slope of the linear regression used as a measure of systolic function. This measures "preload recruitable stroke work" (PRSW) and is discussed by Glower, et al. (*Circulation* 71(5): 994–1009, (1985)). The relationship of end-diastolic pressure to volume is also useful, as an index of diastolic function, when compared to an optimal range. This assessment involves fitting the plot of minimum diastolic pressure against end-diastolic volume to a power function.

The signals derived from this processing can be used alone or in combination within the therapy selected by the physician as explained below.

Once a therapy has been selected by a physician and a particular program stored in the ROM 108 for executing the selected algorithm is activated to increase the strength of ventricular contractions of the heart, the signal is gauged to initiate or continue the appropriate therapy. Alternatives available include various ways of energizing the stimulation pulse generator 150 or activation of a telemetry circuit (Block 160). With some form of cardiac pacing selected (Block 130), appropriate mode and rate control algorithms are activated (Block 132) and pacing pulse patterns are delivered to the heart via pulse generator 150. Energizing the pulse generator can be selected to stimulate cardiac tissue in a variety of ways (135, 136, 137, 138). Alternatively, skeletal muscle can be stimulated (Block 140), utilizing a sequential mode. Energizing of the implanted telemetry circuitry (Block 160) may be done to allow the implanted microprocessor 110 to access an external monitor system 162 or to activate a printer unit 164 to provide a hard copy read-out to the physician. Through the telemetry link, an external drug infusion system 166 can be activated to inject a prescribed dose of a desired medicament into the patient.

As indicated immediately above, several pacing modes are available. These include paired pacing 135, biventricular pacing 136, burst stimulation 137 or intercalated pacing 138. All are focused upon achieving the end result of increasing contractile response of the heart by selective sequencing of stimuli, rather than simply functioning as a cardiac pacemaker by appropriately timing when an intrinsic beat should occur and providing it when such a beat is absent.

The present invention also contemplates that pulse generator 150 may be a dual chamber device. An example of a pacer that may be used in the present invention is provided in U.S. Pat. No. 4,928,688, issued to Mower and assigned to Applicant's assignee. In this pacer, conventional demand pacing circuitry is interconnected to biventricular control circuitry in order to deliver stimuli at two different sites in response to sensed changes in cardiac function for the purpose of augmenting contractile forces of the myocardium. Although directed to control of a demand-type pacer, an example of a control parameter that may be used to supplement the present invention is provided in U.S. Pat. No. 4,773,401, issued to Citak, et al. The Citak, et al. disclosure reveals demand-type circuitry that utilizes as a control parameter the time interval between a systole marker (native QRS or paced beat) and the positive inflection point of the Z v. t signal.

A conventional multielectrode impedance pacing lead, as known in the art, may be used to deliver appropriate pulses to the heart. When selected as the pacing mode, paired pacing (Block 135) will be expected to increase contractile function of the heart, provided the delay between stimuli is appropriately chosen. In this mode, an intrinsic or a paced beat is sensed, then an interval of 150–200 msec is timed before a pacing pulse is delivered to the wall of the right ventricle.

The lead arrangement required for biventricular pacing (Block 136) differs from typical pacer leads. Two lead segments are required, each of which has a stimulation tip electrode for pacing and appropriate sensing electrode(s). One is inserted into the right ventricle, preferably through the superior vena cava, while the second is preferably inserted through the coronary sinus (or into the left ventricle), as described in greater detail in the aforereferenced Mower patent. To augment detection capabilities of the control circuit, it is also preferred to position atrial sense electrodes appropriately. In this manner, the control circuit can refer to both atrial and ventricular depolarizations that are present or absent and respond appropriately through a preset A-V delay timer.

An alternative pacing mode is burst stimulation (Block 137). This technique increases the strength of a myocardial contraction episode via delivery of 1 to 12 stimulating pulses at a frequency of 10 to 130 Hz to a single pacing site or to multiple sites. An example of application of this mode of pacing is disclosed in U.S. Pat. No. 4,865,036, issued to Chirife.

Intercalated pacing (Block 138) is another alternative. In this technique, contractile function of the heart wall is enhanced by extending the relaxation period between beats. In pathologic asynchronous conditions, such as atrial fibrillation, the sequential conduction pattern which exists in individual muscle fibers may be disrupted by delivery of a conducted beat followed by delivery of extrastimuli to the right ventricle at predetermined intervals. Such potentiation functions to extend the relaxation period between beats.

A further rate control algorithm stored in the ROM 108 of microprocessor 110 is utilized to stimulate skeletal muscle (Block 140) using the burst stimulation mode described above. Depending upon the therapeutic rationale implemented, skeletal muscle may be surgically wrapped around the ventricles (Block 142) then stimulated to contract sequentially, as in the manner disclosed in U.S. Pat. No. 4,735,205, issued to Chachques. Skeletal muscle may alternatively be surgically wrapped around an artificial bladder (Block 144), such as an apicoaortic conduit pouch as described by Acker, et al., (*J. Thoracic CV Surgery* 94:163–74 (1987)). Alternatively, it may be applied to an extra-aortic balloon pump as disclosed by Chiu, et al. (*J. Thoracic CV Surgery* 94:694–701 (1987)). In another approach, it may be applied to skeletal muscle tube ventricles or pouches, as described by Stevens, et al. (*J. Surg. Res.* 46:84–89 (1989)).

To condition the skeletal muscle for these applications, synchronization between intrinsic or paced heart activity and skeletal stimulation is programmable from 1:1 to 8:1. The skeletal stimulation consists of a pulse train of 1–12 pulses at a frequency of 10–128 Hz in which spacing between individual pulses can be decremented to increase in frequency as the burst progresses. Programmable "therapy bands" with independent synchrony and delay settings are available to correspond to four different heart rate levels.

By monitoring either systolic or diastolic parameters of the natural or artificial ventricle, as previously described, it is possible to optimize both the rate and mode of stimulation. Since patients requiring these drastic interventions are generally in advanced cardiac failure, their cardiac function is marginal at best and exhibits increased sensitivity to external perturbations (i.e. loading, as in ventricular preload or afterload, etc.). Even though the actual improvement in cardiac function may be small, these patients exist in such a delicate balance that a small improvement in cardiac output can result in a dramatic improvement in the patient's clinical condition.

Cardiac parameters calculated from the implantable device may be transmitted, via telemetry, to an external monitor system as described in U.S. Pat. No. 4,562,841, issued to Brockway, et al. Telemetered parameters may also provide diagnostic information or control to an external drug monitor system.

The telemetry feature of the present invention may utilize a radio frequency data link, as described in the Brockway U.S. Pat. No. 4,562,841 patent or other established approaches now used in the cardiac pacing field. Encoding/decoding circuitry is contained in both an external programmer and in the implantable device. Essentially, symmetric transmission pulses of radio frequency signals in the 100 kHz frequency range are exchanged between these two devices, then formatted into proper sequence and interpreted by I/O controller circuitry. When decoded pulses are received from the implanted device of the present invention, the information is used by a physician to modify the applied electrical therapy. The data transmitted to an external monitor system will typically consist of raw analog information (waveforms) or internally processed digital information. The decoded information is displayed to the physician, in the case of an external monitoring device (Block 162) or printer unit (Block 164), or it is used to modify therapy, in the case of an external drug pump (Block 164).

A typical external monitor system (Block 162) is also described in further detail in the above mentioned Brockway patent. It features a keyboard, display and housing (not shown). The keyboard allows various adjustments in therapy to be communicated transcutaneously to the implanted device. The display visually presents the transmitted analog waveforms as well as textual information. One skilled in the art will recognize that the keyboard may be replaced by other input devices such as touch screen, mouse, scanner, etc. The display may either be a CRT, LCD or plasma panel. A conventional printer unit (Block 164) may be included as a feature of the external monitor.

A drug infusion system (Block 166) capable of interfacing with the present invention is disclosed in U.S. Pat. No. 4,529,401, issued to Leslie and assigned to Applicant's assignee. A microprocessor receives a signal from a telemetry input circuit similar to that contained in the external monitor system and uses the decoded information to control an infusion pump.

The external infusion pump employed is preferably programmable and operates to supply a desired dosage of medicament to a patient in accordance with a desired time profile. It contains encoding/decoding and I/O circuitry to enable receipt and transmission of radio frequency signals via the telemetry circuits employed in the implanted portion of the stimulator of the present invention.

Those skilled in the art will recognize that the apparatus reflected by the block diagrams of FIGS. 1, 2 and 3 may be implemented using all analog circuitry or, alternatively, by incorporating an analog-to-digital converter at the output of the filter and demodulation circuits 48 and 58, the circuits downstream from such an A/D converter can readily be implemented in a programmed microprocessor or microcontroller architecture.

In operation, the physician will evaluate therapy options based on the patient's history and diagnostic workup, including catheterization, electrophysiology, stress testing or other reports. Once a decision is made to implant the monitor/stimulator of the present invention, suitable leads will be selected and the pulse generator of the monitor/stimulator will be programmed to activate those parameters which are particularly applicable to the individual patient. The apparatus will then be implanted and the sensing/pacing lead positioned according to the intended application. At this time, external standards are used to validate the measurements calculated by the device and the selected therapy or therapies will be preliminarily tested. If more than one therapy mode is found to be effective, the physician can elect to establish a decision tree in which alternate modes may be selected to respond to specific ranges of the calculated physiologic values. Alternatively, if a graded response is obtained at different levels of the delivered therapy, an additional decision tree is available to increase or decrease administration of the therapy when the monitored parameters stray from the preset ranges. For example, if increasing the level of pacing output was found to result in a proportional improvement in contraction, it may be desirable to program different levels of output which will be activated as different levels of physiologic need are detected. The testing performed at the time of implant aids the physician in determining these ranges. Thus, criteria for the changes in output and the types of changes to be monitored, in addition to baseline measurements of the selected parameters, are measured and stored in the device's memory 104 at the time of implant. These preprogrammed parameters are treated as baseline measurements during comparisons to subsequently measured parameters. The external monitor system permits some adjustment in these parameters via telemetry. The RAM memory 106 included in microprocessor 110 includes the capability of accumulating functional data over time. When the physician interrogates the apparatus using the external monitor system (Block 162, FIG. 3), trend information is telemetered from the apparatus to the external monitor for assessment by the physician. As with cardiac pacemakers, acute physiological changes, such as normal responses to stress or exertion, are preprogrammed as transient episodes which fall within specified ranges of cardiac parameters to evoke predetermined levels of therapy.

Figure 4:
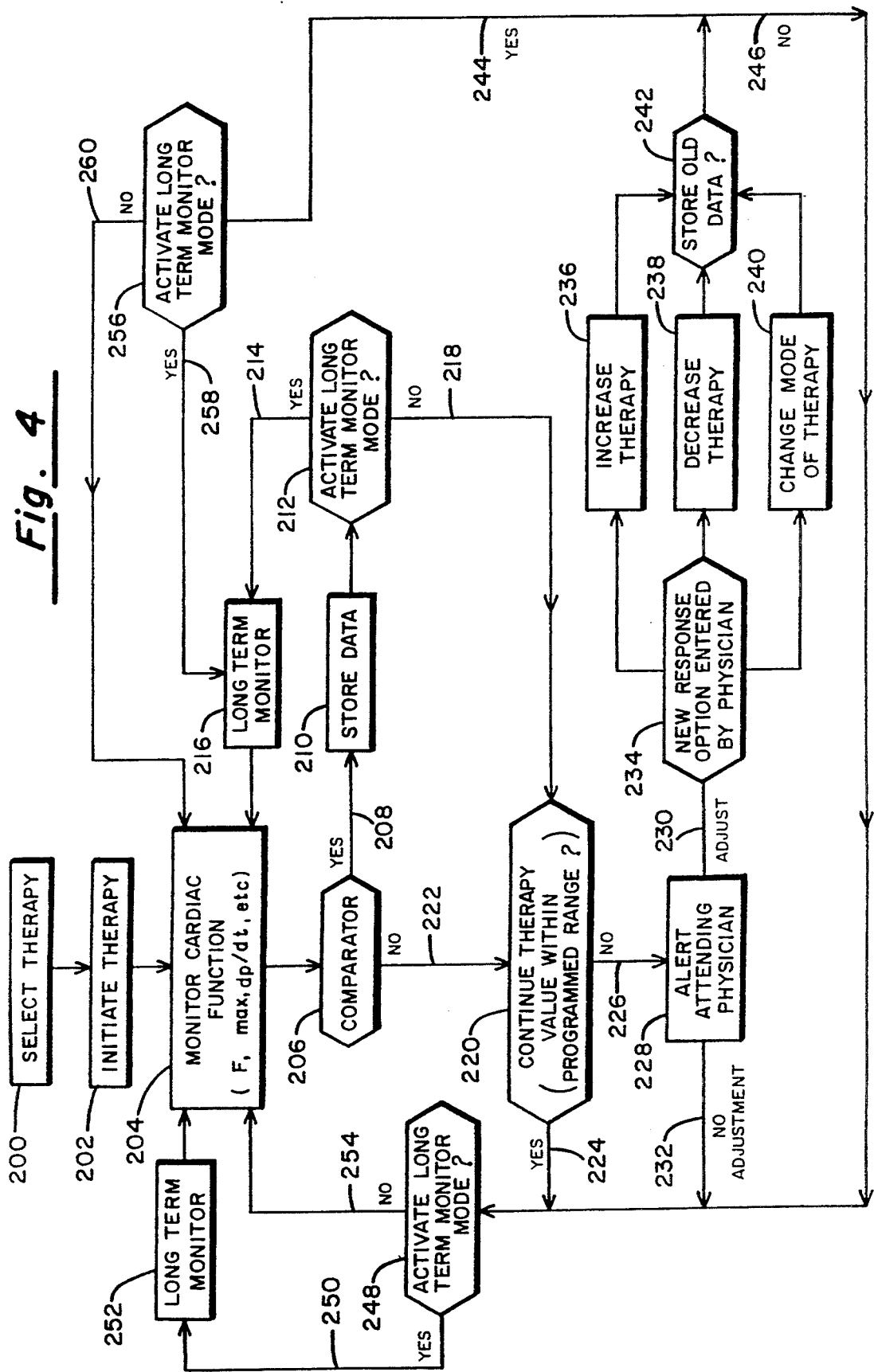
FIG. 4 is a diagram illustrating the "therapy" section of FIG. 1.

FIG. 4 provides a functional block diagram which more fully discloses the therapy selection algorithm represented by block 120 of FIGS. 1 and 3. Referring to block 200, a mode of therapy is externally determined by a physician on the basis of the patient's history and prior diagnostic testing then initiated along with preprogrammed parameter ranges at the time of implant. When a mode of therapy is selected, the device is activated, as at block 202. Upon initiation of therapy, the device begins to monitor the preselected parameters (Block 204) which provide an index of cardiac function. Instantaneous values for these parameters are compared at 206 to predetermined stored values representing desired ranges. Based upon individual preset ranges and levels entered by the physician at block 200, it may be desirable to store the instantaneous values obtained at block 204 as data, as at line 208 and block 210. This data may be in the form of individual values calculated by logic device 60 and microprocessor 110, or accumulated functional data, such as selective samples of electrocardiograms. Under some conditions entered at block 200, it is desirable to monitor and store the calculated parameters at predetermined time intervals (Block 212). When long term monitoring is desirable, as indicated at line 214 and block 216, the function monitor/stimulator will be programmed to periodically reset. When such monitoring is not desired, as at line 218, the function monitor/stimulator is programmed to assess whether to continue therapy (Block 220) based upon criteria input prior to implant (Block 200) or manually by telemetry from the external monitor 162. Alternatively, when calculated values are compared to preset ranges and values (Block 206), there may be no need at this point to store data, as indicated at line 222. Thus, the function monitor/stimulator is programmed to immediately assess whether to continue therapy (Block 220) based upon criteria input prior to implant (Block 200) or manually adjusted by telemetry from the external monitor 162. If the instantaneous value previously calculated at block 204 falls within the preset parameters, the function monitor/stimulator is preprogrammed to return to monitor mode (Block 204), as indicated at line 224. When the calculated value does not fall within a preset range or parameter, as indicated at line 226, the physician will be alerted, as indicated at block 228. This may be accomplished in a variety of ways available to one skilled in the art, among which a telemetered signal to a printer unit 164 is preferred. In response to the physician alert at block 228, the physician may desire to enter an adjustment in therapy (Line 230) or maintain the present preprogrammed criteria (Line 232). When an adjustment in therapy criteria is desired, the physician will initiate an appropriate response as at block 234. The physician may choose to increase the present mode of therapy (Block 236), decrease the present mode of therapy (Block 238) or he may desire to activate a different mode of therapy (Block 240). Regardless of which option is selected, at this time it may be desirable to store the calculated instantaneous values as data (Block 242). Whether stored (Line 244) or not stored (Line 246), the function monitor/stimulator is preprogrammed to be reset by returning to block 204 to monitor all presently preselected parameters. As indicated at blocks 248 and 256, the function monitor/stimulator is also preprogrammed to assess whether a long-term monitor mode was activated by the physician at block 234. If this mode is selected, as indicated at line 250 and block 252 or line 258 and block 216, instantaneous values of cardiac function parameters will be intermittently sampled according to a preprogrammed algorithm. If this mode is not activated, as indicated at lines 254 or 260, the function monitor/stimulator is programmed to reset to monitor cardiac function (Block 204) in the presently programmed manner.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. Apparatus for applying therapy to a patient based upon a contractile state of the patient's heart, the apparatus comprising:
   (a) intracardiac sensing means for sensing hemodynamic indicators of said contractile state in at least one ventricular chamber of the heart;
   (b) signal means coupled to said sensing means for developing a control signal varying as a function of said hemodynamic indicators;
   (c) patient therapy means having at least one stimulating electrode for applying stimulating pulses to tissue as a function of said control signal to increase the strength of contraction of the patient's heart; and
   (d) means for applying said control signal to said patient therapy means for changing said contractile state by increasing the strength of contraction of the heart.

2. The device as in claim 1 wherein said intracardiac sensing means comprises:
   pressure sensing means for sensing the pressure in at least one ventricular chamber of the heart and producing a pressure control signal as said control signal, and said pressure control signal varies as a function of said pressure due to the beating action of the heart.

3. The device as in claim 1 wherein said intracardiac sensing means comprises:
   (a) volume sensing means for sensing ventricular volume in at least one ventricular chamber of the heart; and
   (b) intracardiac pressure sensing means for sensing pressure in at least one ventricular chamber of the heart;
and signal means comprising:
   (c) first control signal means coupled to said volume sensing means for developing a first control signal varying as a function of said ventricular volume; and
   (d) second control signal means coupled to said intracardiac pressure sensing means for developing a second control signal varying as a function of said pressure, whereby said patient therapy means applies said stimulating pulses to said tissue as a function of said first and second control signals by increasing said contractile state in relation to said changes in said ventricular volume and said pressure.

4. The device as in claim 1 further including calculating means for calculating an ejection fraction, wherein said patient therapy means receives a further control signal varying as a function of the ejection fraction, wherein ejection fraction is computed by said calculating means by dividing a control signal value selected to indicate stroke volume by a control signal value selected to indicated end-diastolic volume.

5. The device as in claim 1 further including means for calculating cardiac output and means for determining heart rate, wherein said patient therapy means receives and responds to a further control signal varying as a function of the cardiac output, wherein cardiac output is calculated as the product of a control signal value selected to indicate the sensed heart rate times a control signal value selected to indicate stroke volume.

6. The device as in claim 2 wherein said signal means includes:
 (a) means for producing a time varying signal proportional to pressure measured in one cardiac chamber due to the beating action of the heart;
 (b) means for extracting from said time varying signal a modulation signal due to pressure changes in said cardiac chamber; and
 (c) means for producing the pressure control signal from said modulation signal which, when applied to said patient therapy means, results in change in the heart's contractile state by increasing the strength of contraction of the heart.

7. The device as in claim 1, wherein said signal means is comprised of means for developing an impedance control signal, comprising:
 (a) means for producing a time varying signal proportional to impedance measured in one cardiac chamber due to beating action of the heart;
 (b) means for extracting from said time varying signal a modulation signal due to impedance changes in said cardiac chamber; and
 (c) means for producing the impedance control signal from said modulation signal, whereby said therapy means changes the heart's contractile state as a function of said impedance control signal by increasing the strength of contraction of the heart.

8. The device as in claim 3, further including:
 (a) a microprocessor for computing the area inside a curve obtained by integration of a plot of the pressure as a function of the ventricular volume, as an indicator of stroke work;
 (b) means coupled to said microprocessor for developing a stroke work control signal varying as a function of said stroke work; and
 (c) means for applying said stroke work control signal to said patient therapy means, for changing said contractile state.

9. The device in claim 3, further including:
 (a) a microprocessor for computing the slope of a regression line plotted through maximal pressure/volume points taken at endsystole of the cardiac cycle, as an indicator of ejection phase contractility;
 (b) means coupled to said microprocessor for developing an ejection phase control signal varying as a function of said indicator of ejection phase contractility; and
 (c) means for applying said ejection phase control signal to said patient therapy means, for changing said contractile state.

10. The device as in claim 3, further including:

(a) a microprocessor for computing a curve resulting from a plot of minimum diastolic pressure against end-diastolic volume, as an indicator of diastolic function;
 (b) means coupled to said microprocessor for developing a diastolic function control signal varying as a function of said curve; and
 (c) means for applying said diastolic function control signal to said patient therapy means, for changing said contractile state.

11. The device as in claim 1, wherein said patient therapy means further includes:
 (a) means for applying said stimulating pulses from said stimulating electrode to the heart in a predetermined pattern for increasing the strength of contraction of said heart, wherein said predetermined pattern of stimulating pulses includes a pair of pulses, said pair comprising delivery of a first pulse that is either intrinsic or paced, followed by a delay in a range of 150 to 200 msec, then delivery of a second pulse in the form of a pacing pulse, delivered to the right ventricle of the heart, to increase the strength of contraction of said heart.

12. The device as in claim 1, wherein said patient therapy means further includes:
 (a) means for applying said stimulating pulses from said stimulating electrode to the heart in a predetermined pattern for increasing the strength of contraction of said heart, wherein said predetermined pattern of said stimulating pulses includes multichamber pacing, said multichamber pacing pattern including delivering either simultaneous or temporarily spaced pacing pulses to two or more sites within the chambers of the heart to increase the strength of contraction or to improve the chamber coordination of said heart.

13. The device as in claim 1 wherein said patient therapy means further includes:
 (a) means for applying said stimulating pulses from said stimulating electrode to at least one site in the heart in a predetermined pattern for increasing the strength of contraction of said heart, wherein said predetermined pattern of said stimulating pulses includes a burst pattern, said burst pattern including delivering from 1 to 12 said stimulating pulses at a frequency in the range of from 10 to 130 Hz.

14. The device as in claim 1 wherein said patient therapy means further includes:
 (a) means for applying said stimulating pulses from said stimulating electrode to the heart in a predetermined pattern for increasing the strength of contraction of said heart, wherein said predetermined pattern of said stimulating pulses includes a pattern of intercalated pacing, comprising delivery of at least one extrastimulus to the right ventricle;
 (b) delay means for calculating a delay of a preset interval after said intracardiac sensing means detects the presence of a conducted heartbeat; and
 (c) means for developing an intercalated control signal for causing said patient therapy means to deliver at least one extrastimulus to the right ventricle, thereby extending a relaxation period of the heart to enhance the strength of contraction of said heart.

15. The device as in claim 1 wherein said patient therapy means further includes:
 (a) skeletal muscle stimulating means for applying a predetermined pattern of said stimulating pulses from said stimulating electrode to a skeletal muscle that has been surgically attached to the heart, for increasing the strength of contraction of said heart.

16. The device as in claim 1 wherein said means for applying said control signal to said patient therapy means further includes telemetry means for transmitting and receiving radio frequency encoded signals.

17. Apparatus for applying therapy to a patient based upon a contractile state of the patient's heart, the apparatus comprising:
   (a) intracardiac sensing means for sensing hemodynamic indicators of said contractile state in at least one ventricular chamber of the heart;
   (b) signal means coupled to said sensing means for developing a control signal varying as a function of said hemodynamic indicators;
   (c) a drug infusion system for administering a drug to the patient as a function of said control signal to increase the strength of contraction of the patient's heart; and
   (d) means for applying said control signal to said drug infusion system for changing said contractile state by increasing the strength of contraction of the heart.

18. A method of applying therapy to a patient, using an apparatus comprising:
   (a) intracardiac sensing means for sensing hemodynamic indicators of a contractile state of a patient's heart;
   (b) signal means coupled to said sensing means for producing a control signal in response to the sensed hemodynamic indicators; and
   (c) patient therapy means comprising either (i) a stimulating electrode for applying stimulating pulses to tissue as a function of said control signal for increasing the strength of contraction of the patient's heart, or (ii) a drug infusion system for administering a drug to the patient to increase the contractile strength of the patient's heart;
comprising the steps of:
   (i) sensing said hemodynamic indicators using said intracardiac sensing means;
   (ii) using said signal means to produce a control signal in response to the sensed hemodynamic indicators; and
   (iii) applying therapy to the patient using said therapy means by applying said stimulating pulses to said tissue, or using said drug infusion system to administer said drug to said patient, to increase the strength of contraction of the patient's heart.

* * * * *